United States Patent
Ghosh et al.

(10) Patent No.: US 7,084,318 B2
(45) Date of Patent: Aug. 1, 2006

(54) TOLUENE METHYLATION PROCESS

(75) Inventors: Ashim Kumar Ghosh, Houston, TX (US); Pamela Harvey, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 239 days.

(21) Appl. No.: 10/632,254

(22) Filed: Aug. 1, 2003

(65) Prior Publication Data

US 2005/0027151 A1 Feb. 3, 2005

(51) Int. Cl.
*C07C 2/66* (2006.01)
(52) U.S. Cl. ...................................... 585/467
(58) Field of Classification Search ................. 585/467
See application file for complete search history.

(56) References Cited

U.S. PATENT DOCUMENTS

| | | |
|---|---|---|
| 3,702,886 A | 11/1972 | Argauer et al. |
| 3,965,207 A | 6/1976 | Weinstein |
| 4,278,827 A | 7/1981 | Chu et al. |
| 4,548,914 A | 10/1985 | Chu |
| 4,590,321 A | 5/1986 | Chu |
| 4,623,530 A | 11/1986 | Cullo et al. |
| 4,623,533 A | 11/1986 | Young |
| 4,638,106 A | 1/1987 | Pieters et al. |
| 4,665,251 A | 5/1987 | Chu |
| 4,670,616 A | 6/1987 | De Simone et al. |
| 4,673,767 A | 6/1987 | Nimry et al. |
| 4,694,114 A | 9/1987 | Chu et al. |
| 4,695,666 A | 9/1987 | Chao et al. |
| 4,695,667 A | 9/1987 | Sumitani et al. |
| 4,704,495 A | 11/1987 | Dessau |
| 4,716,135 A | 12/1987 | Chen |
| 4,721,827 A | 1/1988 | Cullo et al. |
| 4,727,209 A | 2/1988 | Chao |
| 4,746,763 A | 5/1988 | Kocal |
| 4,758,328 A | 7/1988 | Young |
| 4,761,513 A | 8/1988 | Steacy |
| 4,847,223 A | 7/1989 | Le Van Mao et al. |
| 4,861,930 A | 8/1989 | Cottrell et al. |
| 4,873,067 A | 10/1989 | Valyocsik et al. |
| 4,891,197 A | 1/1990 | Derouane et al. |
| 4,891,467 A | 1/1990 | Sikkenga |
| 4,902,406 A | 2/1990 | Valyocsik |
| 4,912,073 A | 3/1990 | Chu |
| 4,914,067 A | 4/1990 | Pellet et al. |
| 4,935,574 A | 6/1990 | D'Amore et al. |
| 4,962,255 A | 10/1990 | Fraenkel et al. |
| 4,973,781 A | 11/1990 | Valyocsik et al. |

(Continued)

OTHER PUBLICATIONS

Kaeding, W.W., et al., Selective Alkylatioin of Toluene to Produce para-Xylene, Journal of Catalysis 67, 1981, pp. 159-174, no month.

(Continued)

*Primary Examiner*—Elizabeth D. Wood
(74) *Attorney, Agent, or Firm*—Grady K. Bergen; Jim D. Wheelington

(57) ABSTRACT

A method of preparing a xylene product is carried out in a reactor containing a phosphorus-treated ZSM-5-type zeolite catalyst. The method includes initiating a unique start-up of a toluene methylation reaction by contacting the catalyst with a toluene/methanol feed and a cofeed of hydrogen introduced into the reactor at certain start-up conditions. By utilizing the start-up conditions high selectivity for p-xylene can be achieved while providing stable catalytic activity over extended periods.

23 Claims, 2 Drawing Sheets

U.S. PATENT DOCUMENTS

| | | |
|---|---|---|
| 5,041,402 A | 8/1991 | Casci et al. |
| 5,043,502 A | 8/1991 | Martindale et al. |
| 5,047,141 A | 9/1991 | Chu |
| 5,068,483 A | 11/1991 | Barthomeuf et al. |
| 5,094,995 A | 3/1992 | Butt et al. |
| 5,105,047 A | 4/1992 | Waller |
| 5,108,579 A | 4/1992 | Casci |
| 5,110,776 A | 5/1992 | Chitnis et al. |
| 5,124,299 A | 6/1992 | Waller |
| 5,171,921 A | 12/1992 | Gaffney et al. |
| 5,173,461 A | 12/1992 | Absil et al. |
| 5,178,748 A | 1/1993 | Casci et al. |
| 5,210,356 A | 5/1993 | Shamshoum et al. |
| 5,227,558 A | 7/1993 | Shamshoum et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |
| 5,336,478 A | 8/1994 | Dwyer et al. |
| 5,336,824 A | 8/1994 | Shamshoum et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,387,732 A | 2/1995 | Shamshoum et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,766 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,847,255 A | 12/1998 | Ghosh et al. |
| 5,902,919 A | 5/1999 | Chen et al. |
| 5,905,051 A | 5/1999 | Wu et al. |
| 5,907,073 A | 5/1999 | Ghosh |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,990,031 A | 11/1999 | Ghosh |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,057,485 A | 5/2000 | Merrill et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,866 A | 7/2000 | Drake et al. |
| 6,090,274 A | 7/2000 | Wu et al. |
| 6,090,991 A | 7/2000 | Butler et al. |
| 6,096,938 A | 8/2000 | Ghosh |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,222,084 B1 | 4/2001 | Ghosh et al. |
| 6,251,263 B1 | 6/2001 | Hatanaka et al. |
| 6,268,305 B1 | 7/2001 | Butler et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,008 B1 | 10/2002 | Ou et al. |
| 6,469,095 B1 | 10/2002 | Garelss et al. |
| 6,503,862 B1 | 1/2003 | Yamamoto |
| 6,504,072 B1 | 1/2003 | Brown et al. |
| 6,504,074 B1 | 1/2003 | Verduijn et al. |
| 6,506,954 B1 | 1/2003 | Brown et al. |
| 6,518,213 B1 | 2/2003 | Yamamoto et al. |
| 6,548,725 B1 | 4/2003 | Froment et al. |
| 6,566,293 B1 | 5/2003 | Vogt et al. |
| 6,589,901 B1 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B1 | 2/2004 | Williams et al. |
| 6,699,811 B1 | 3/2004 | Mohr et al. |
| 6,723,297 B1 | 4/2004 | Chen et al. |
| 6,726,834 B1 | 4/2004 | Quesada et al. |
| 6,770,251 B1 | 8/2004 | Yoshikawa |
| 6,773,694 B1 | 8/2004 | Lesch et al. |
| 6,799,089 B1 | 9/2004 | Toulhoat |
| 6,811,684 B1 | 11/2004 | Mohr et al. |
| 6,812,181 B1 | 11/2004 | van der Berge et al. |

OTHER PUBLICATIONS

Hibino, T., et al., Shape-Selectivity Over HZSM-5 Modified by Chemical Vapor Deposition of Silicon Alkoxide, Journal of Catalysis 128, 1991, pp. 551-558, no month.

Yashima, T., et al., Selective Formation of p-Xylene by Alkylation of Toluene with Methanol on ZSM-5 Type Zeolites, Stud. Surf. Sci. Catal., 1981, 7, pp. 739-751, no month.

Sayed, M. B., et al., The Effect of Modification with Boron on the Catalytic Activity and Selectivity of HZSM-5, Journal of Catalysis 101, 1986, pp. 43-55, no month.

Kim, J.-H, et al., Generation of Shape-Selectivity of p-Xylene Formation in the Synthesized ZSM-5 Zeolites, Journal of Catalysis 173, 1998, pp. 433-439, no month.

Vinek, H., et al., Production and Reactions of Xylenes over H-ZSM-5, Journal of Molecular Catalysis, 64, 1991, pp. 23-39, no month.

Chen, N.Y., Reactions of Mixtures of Toluene and Methanol Over ZSM-5, Journal of Catalysis 114, 1988, pp. 17-22, no month.

Young, L.B., et al., Shape Selective Reactions with Zeolite Catalysts, Journal of Catalysis 76, 1982, pp. 418-432, no month.

Nirula, S.C., Para-Xylene From Toluene and Methanol, Process Economics Program, 1983, pp. 1-23, SRI International, Menlo Park, Ca, no month.

Wang, I., et al., Para-selectivity of Diaklybenzenes over Modified HZSM-5 by Vapour Phase Deposition of Silica, Applied Catalysis, 54, 1989, 257-266, no month.

Das, J., et al., Ethylbenzene Dealkylation and Realkylation over Pore Size Regulated MFI Zeolite, Ind. Eng. Chem. Res., 32, 1993, pp. 2525-2529, no month.

Kim, J.-H., et al., Para-selectivity of Metallosilicates with MFI Zeolite Structure Zeolites, vol. 11, 1991, pp. 59-63, no month.

Kim, J.-H., et al., Preparation of Highly Para-selective Metallosilicate Catalysts for Alkylation of Ethylbenzene with Ethanol, Applied Catalysis A:100, 1993, pp. 27-36, no month.

TOLUENE METHYLATION PROCESS

TECHNICAL FIELD

The invention relates generally to the alkylation of aromatic compounds.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene production. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

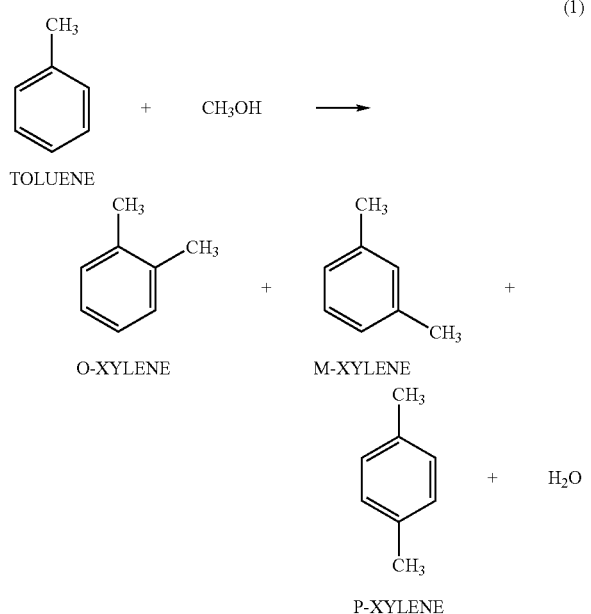

Thermodynamic equilibrium compositions of o-, m-, and p-xylenes may be around 25, 50 and 25 mole %, respectively, at a reaction temperature of about 500° C. Such toluene methylation may occur over at wide range of temperatures, however. Byproducts such C9+ and other aromatic products can be produced by secondary alkylation of the xylene product.

Para-xylene can be separated from mixed xylenes by a cycle of adsorption and isomerization. Such cycle may have to be repeated several times because of the low isomeric concentration in the equilibrium mixture. A high purity grade (99+%) p-xylene is desirable for its oxidation to terephthalic acid process. The production cost for such a high purity grade p-xylene can be very high, however. A different method that employs crystallization techniques can be used and may be less expensive where the concentration of p-xylene is around 80% or higher in the initial xylene product. Thus, higher than equilibrium concentrations of p-xylene may be desirable.

A significantly higher amount of p-xylene can be obtained in toluene methylation if the catalyst has shape selective properties. Shape selective properties can be obtained in modified zeolite catalyst by narrowing zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

In Kaeding, et al, *Selective Alkylation of Toluene with Methanol to Produce para-Xylene*, Journal of Catalysis, Vol. 67, pp. 159–174 (1981), a procedure of making a ZSM-5 catalyst by incorporating 5% phosphorus was described in which the catalyst was impregnated with a solution of diphenylphosphinous acid in toluene. The ZSM-5 catalyst thus modified showed toluene methylation activity with 84–90% para isomer in xylene product. In another procedure, a catalyst was modified by incorporating 8.51% phosphorus from an aqueous phosphoric acid reagent. The catalyst showed p-xylene selectivity as high as 97%, however, the catalyst showed a decreasing activity within hours due to coke deposition.

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

Figure 1:
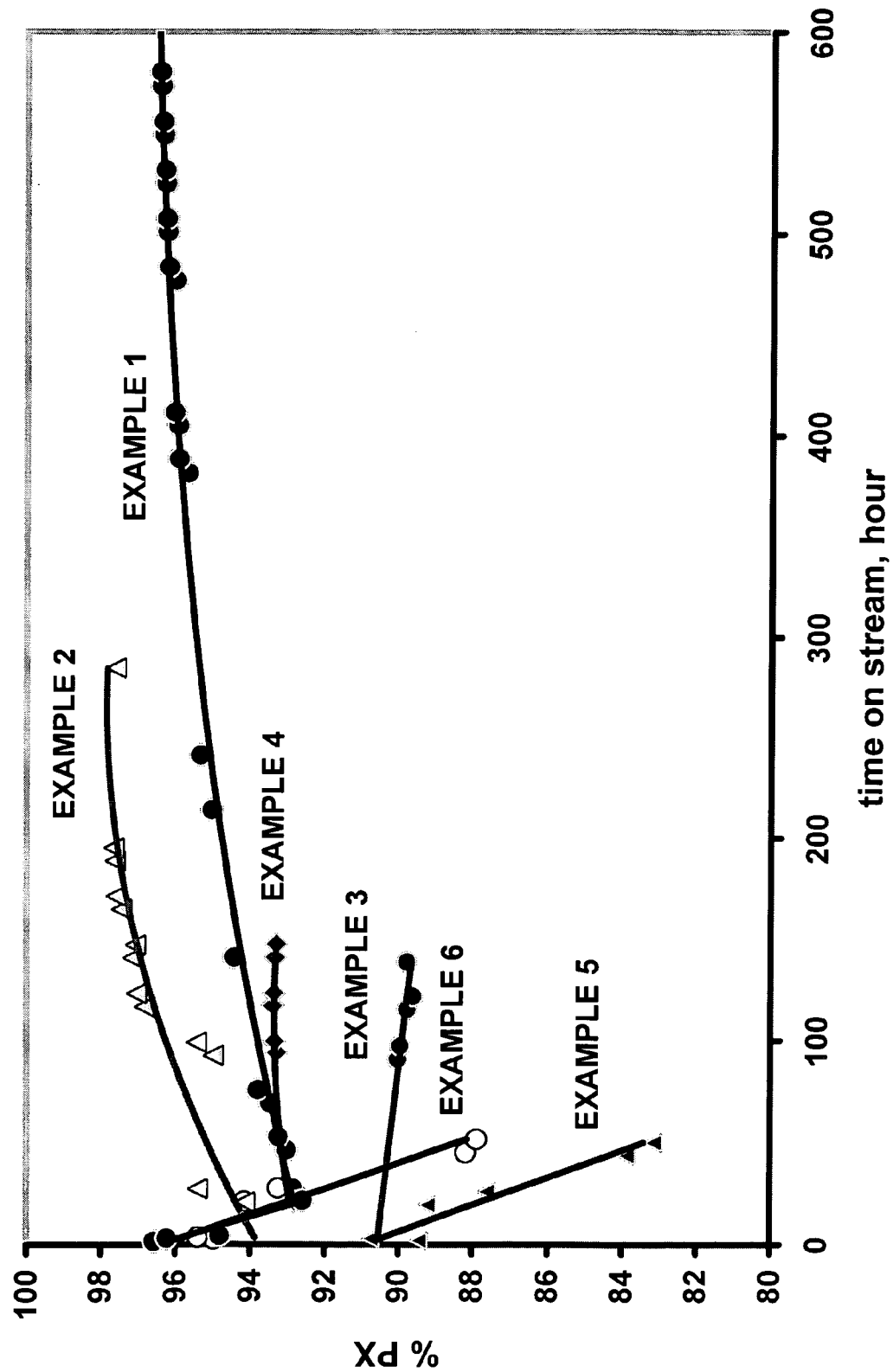
FIG. 1 is a plot of para-xylene selectivity over time for Examples 1–6.

Modification of ZSM-5-type zeolite catalysts with phosphorus-containing compounds has been shown to yield significantly greater amounts of p-xylene than the thermodynamic equilibrium value in toluene methylation using unmodified catalysts. Such modification has been shown to provide selectivity for p-xylenes of greater than 80%. Although such phosphorus-treated ZSM-5 catalysts may have a high selectivity for p-xylene, they tend to deactivate at a very fast rate, for example, the catalyst may lose greater than 50% of its initial activity within a day. This may possibly be due to coke deposition on the catalyst.

As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense. As used herein, catalytic activity can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for total xylenes may be expressed as:

$$\text{Mole \% Total Xylene Selectivity} = [X_{tx}/(T_i - T_o)] \times 100 \quad (3)$$

where, $X_{tx}$ is the number of moles of total (o-, m- or p-) xylenes in the product. As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene.

It has been discovered that particular start-up conditions provide stable activity of the phosphorus-treated ZSM-5-type zeolite catalysts, while still maintaining high selectivity for p-xylene in the methylation of toluene. As used herein, "stable activity" may be defined as less than a 0.20 mole % average loss in conversion per day with less than a 5% decrease in p-xylene selectivity given constant temperature conditions. In particular, stable activity can be maintained for 25, 50, 100, 500, 700 or 1000 hours or more after start-up of the methylation reaction while still maintaining or even increasing selectivity for p-xylene. Typical selectivity for p-xylene may be from about 80%, 85%, 90% by total moles of xylene or more, with from about 95% by total moles xylene or more being readily obtainable.

The ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of from 25 to 300, more particularly from about 30 to about 280 prior to modification. The ZSM-5 may be modified by treating with phosphorus-containing compounds such as phosphoric acid ($H_3PO_4$) and ammonium hydrogen phosphate (($NH_4$)$_2HPO_4$) to provide a catalyst for toluene methylation with shape selective properties to give high p-xylene concentration. Such modified catalysts may contain phosphorus in an amount of from about 0.01 to about 0.15 g P/g zeolite, more particularly from about 0.02 to about 0.13 g P/g zeolite. The phosphorus-modified zeolite may be calcined at temperature of about 500 to 570° C. The catalyst may have a BET surface area of 170–200 m$^2$/g and pore volume in the range of 0.10–0.18 ml/g catalyst. The catalyst may have weak acidity showing broad peak(s) with peak maxima between 250° C. and 350° C., as characterized by ammonia temperature programmed desorption ($NH_3$-TPD) technique.

The novel start-up procedure includes particular conditions or combination of conditions. These include a toluene/methanol feed to the reactor containing the phosphorus-treated ZSM-5 catalyst to provide an initial liquid hourly space velocity (LHSV) of from about 1 hr$^{-1}$ to about 50 hr$^{-1}$, more particularly from about 1 to about 35 hr$^{-1}$. The toluene and methanol feed may be premixed prior to introduction into the reactor as a single mixed feed stream. The liquid feed may also contain small quantities of water, C9+ aromatics and other compounds. The liquid hour space velocities presented herein, however, are based upon a toluene/methanol feed without the inclusion of any other components. The toluene/methanol molar ratio in the feed can range from 0.5 to 10.0, more particularly 1.0 to 5.0. Additionally, an initial cofeed of hydrogen gas ($H_2$) is provided at a hydrogen/hydrocarbon ($H_2$/HC) molar ratio of less than about 8, more particularly from about 0.1 to about 8. Unless otherwise noted, all $H_2$/HC ratios presented herein are molar ratios. The final reactor temperature of from about 500° C. to about 700° C. is provided at startup.

The reaction is typically carried out in a continuous flow-type reactor. Single or multi reactors in series and/or parallel are suitable for carrying out the reaction. During start-up, the reactor temperature can be gradually increased. Initially, upon introduction of feed into the reactor, the reactor temperature may be about 200° C. or above. The temperature may then be increased to the final desired temperature. This temperature may be increased gradually at a rate of from about 1° C./min to about 10° C./min to provide a final start-up reactor temperature of from about 500° C. to about 700° C.

Such start-up conditions are maintained from one-half to about 20 hours, more particularly from about 45 minutes to 5 hours, and more particularly from about 1 to 3 hours. Thereafter, the conditions are adjusted to "run conditions" for steady toluene conversion and selectivity to total xylenes and p-xylene. Such adjustments include LHSV reduction to about 10 hr$^{-1}$ or less, more particularly, from about 5 hr$^{-1}$ or less, and still more particularly from about 1 to about 3 hr$^{-1}$. Additionally, the hydrogen cofeed is adjusted to an $H_2$/HC molar ratio of at least 1 or more, more particularly from about 2 to about 8, and still more particularly from about 5 to about 8. The temperature may also be maintained at from about 500° C. to about 700° C. during run conditions. Such start-up conditions provide significant enhancement in p-xylene selectivity of about 80%, 90%, 95% or above.

The reactor pressure may remain generally constant during both start-up and normal run stages. The reactor pressure typically ranges from about 10 to about 50 psig, more particularly from about 20 to about 50 psig.

The following examples better serve to illustrate the invention.

EXAMPLES

The reactions in the following examples were carried out in a single flow-type reactor, as described further below, in a downflow mode wherein the toluene and methanol were premixed prior to introduction into the reactor. The phosphorus-treated ZSM-5 zeolite catalyst used in the following examples for toluene methylation had a silica/alumina ($SiO_2/Al_2O_3$) mole ratio of about 280 prior to phosphorus treatment. In Examples 1–6, an ammonium ion-exchanged ZSM-5 zeolite was modified using ammonium hydrogen phosphate (AHP), ($NH_4$)$_2HPO_4$, by first preparing a slurry of the ZSM-5 zeolite in deionized water. The slurry was then heated to about 80° C. and to this was added the AHP (0.24 g AHP/g of ZSM-5 powder). The mixture was then heated to approximately 100° C. in order to evaporate all water. The resulting zeolite was then dried in an oven overnight at a temperature at about 90 to 120° C. The dried zeolite was then calcined in air at a temperature of about 530° C. No binder was used to form the catalyst. The modified ZSM-5 was sized to form a 20–40 mesh for toluene methylation reaction. The final catalyst thus synthesized possessed the following properties: BET surface area about 190 m$^2$/g, pore volume about 0.139 ml/g, average pore diameter about 29 Å. Examples 5–6 are comparative examples.

In examples 1–6, the reactor consisted a stainless steel tube having a diameter of approximately ½-inch. A catalyst charge ranging from 1.35 ml to 5.4 ml, typically 2.70 ml, was placed within the tubular reactor at about its midpoint. Layers of inert material such as silicon carbide, SiC, were added to both ends of the catalyst bed. The feed was made by mixing toluene and methanol at a desired ratio. The feed was then pumped at a predetermined rate. $H_2$ gas was added to the feed at a predetermined rate to maintain a selected $H_2$/HC ratio.

Example 1

A catalyst charge of 2.70 ml was loaded in the reactor. The catalyst was dried at 200° C. under $H_2$ flow for at least 1 hour prior to feed introduction. The reactor pressure was maintained at 20 psig. The toluene/methanol premixed feed with a 1/1 mole ratio was introduced at a rate of about 1.445 ml/min giving an LHSV of about 32 $hr^{-1}$. The cofeed $H_2$ was used at 50 cc/min giving $H_2$/HC mole ratio of about 0.1. The catalyst bed inlet temperature was slowly increased (10° C./min) and adjusted to about 600° C. After initial 1 hour time on stream, the operating conditions were adjusted to run conditions. The feed rate was decreased to about 0.089 ml/min giving LHSV of about 2 $hr^{-1}$. Also, $H_2$ cofeed gas rate was increased from 50 cc/min to 223 cc/min to maintain $H_2$/HC mole ratio of about 7. The reactor start-up and run operating conditions and toluene conversion and p-xylene selectivity are summarized in Tables 1A and 1B.

TABLE 1A

|  | Start-Up Conditions | Run Conditions |
|---|---|---|
| Temperature | 600° C. | 600° C. |
| Feed Toluene/Methanol Mole Ratio | 1:1 | 1:1 |
| LHSV, $hr^{-1}$ | 32 | 2 |
| H2/HC mole ratio | 0.1 | 7 |

TABLE 1B

| Time on Stream, hr | % Toluene Conversion | % p-Xylene Selectivity |
|---|---|---|
| 1.83 | 18.79 | 96.57 |
| 3.33 | 12.65 | 96.23 |
| 4.33 | 13.87 | 94.80 |
| 21.83 | 16.43 | 92.58 |
| 27.83 | 12.27 | 92.86 |
| 46.33 | 12.12 | 93.02 |
| 52.83 | 19.97 | 93.23 |
| 69.33 | 16.18 | 93.47 |
| 75.83 | 16.61 | 93.79 |
| 141.33 | 16.52 | 94.43 |
| 241.58 | 15.21 | 95.33 |
| 381.83 | 20.58 | 95.69 |
| 388.83 | 19.75 | 95.93 |
| 411.83 | 19.65 | 96.05 |
| 501.40 | 19.40 | 96.25 |
| 555.83 | 17.27 | 96.37 |
| 651.83 | 23.75 | 96.55 |
| 699.83 | 17.61 | 96.60 |
| 723.83 | 22.25 | 96.59 |
| 747.83 | 17.67 | 96.64 |
| 813.33 | 17.45 | 96.68 |
| 861.33 | 22.91 | 96.68 |
| 885.33 | 22.24 | 96.74 |
| 909.33 | 16.30 | 96.74 |
| 981.33 | 16.33 | 96.78 |
| 987.83 | 15.32 | 96.79 |

Figure 2:
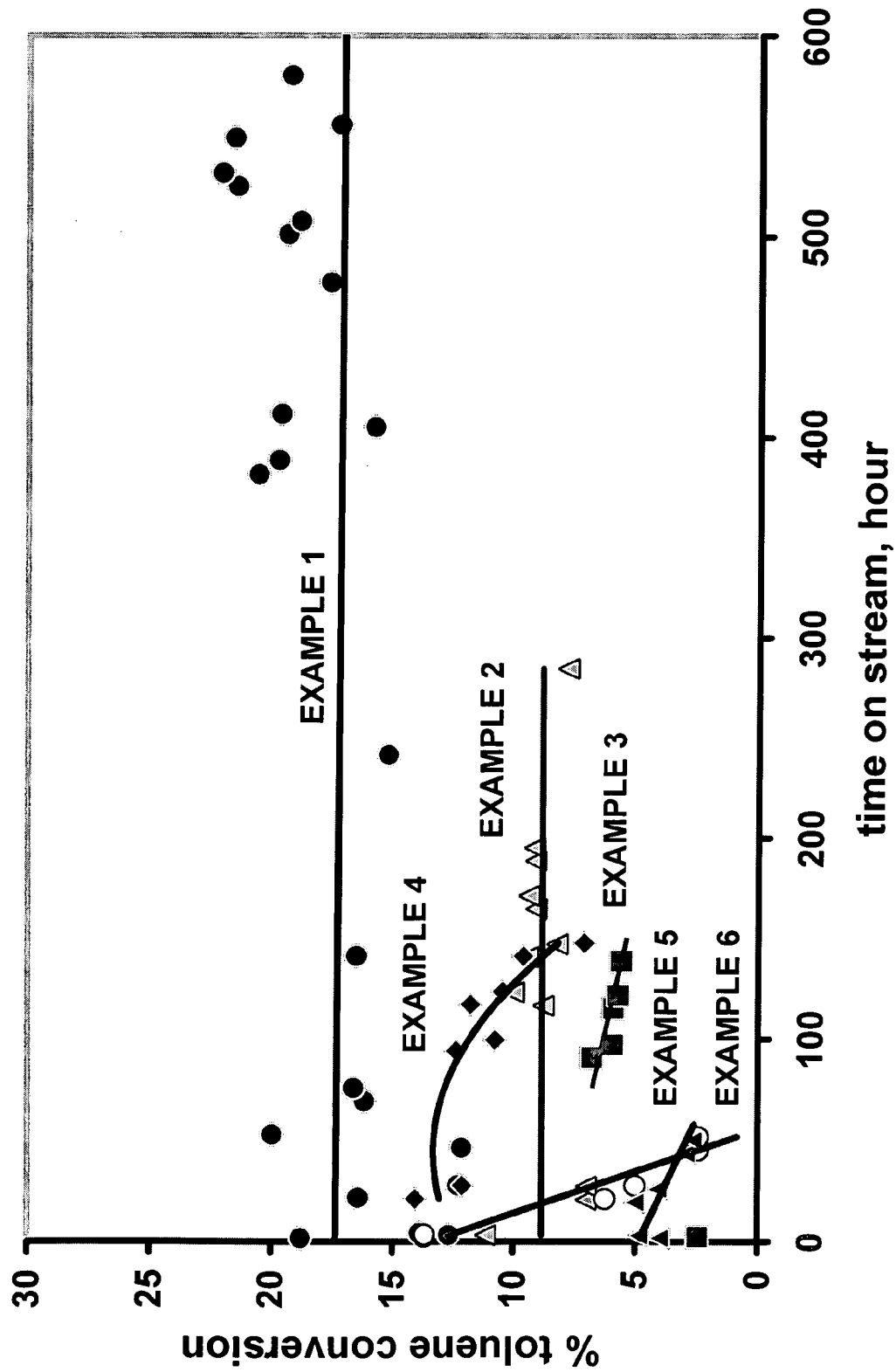
FIG. 2 is a plot of toluene conversion over time for Examples 1–6.

As can be seen in FIGS. 1 and 2, for Example 1, the level of selectivity for p-xylene remained fairly stable. The p-xylene selectivity at the start-up was above 96%, then it decreased to nearly 92% during the first 28 hours or so and then gradually increased to above 96% in the first 500 hours, and further increased to about 97% during 500–1000 hours time on stream. The conversion remained stable for the 1000 hours tested with an average conversion of about 17.35 mole %. The toluene conversion (y) versus the time on stream (x) shows the following linear equation: y=−0.0004x+17.35, suggesting about 0.0004% conversion decrease per hour.

Example 2

A catalyst charge of 2.70 ml was loaded in the reactor. The catalyst was dried at 200° C. under $H_2$ flow for at least 1 hour prior to feed introduction. The reactor pressure was maintained at 20 psig. The toluene/methanol premixed feed with 2/1 mole ratio was introduced at a rate of about 0.101 ml/min giving an LHSV of about 2 $hr^{-1}$. The cofeed $H_2$ was used at 51 cc/min giving $H_2$/HC mole ratio of about 1.6. The catalyst bed inlet temperature was slowly increased (10° C./min) and adjusted to 600° C. After an initial 27 hours time on stream, the cofeed $H_2$ rate was increased from 51 cc/min to 223 cc/min giving $H_2$/HC mole ratio of 7.8. After about 99 hours time on stream the cofeed $H_2$ rate was decreased from 223 cc/min to 51 cc/min giving $H_2$/HC mole ratio of about 1.7. By decreasing the $H_2$/HC mole ratio from about 7.8 to 1.7 the toluene conversion improved. The reactor start-up and normal operating conditions and toluene conversion and p-xylene selectivity are summarized in Tables 2A and 2B.

TABLE 2A

|  | Start-Up Conditions | Run Conditions (until 27 hr) | Run Conditions (27–99 hr) | Run Conditions (99–285 hr) |
|---|---|---|---|---|
| Temperature | 600° C. | 600° C. | 600° C. | 600° C. |
| Feed Toluene/Methanol Mole Ratio | 2:1 | 2:1 | 2:1 | 2:1 |
| LHSV, $hr^{-1}$ | 2 | 2 | 2 | 2 |
| H2/HC mole ratio | 1.6 | 1.6 | 7.8 | 1.7 |

TABLE 2B

| Time on Stream, hr | % Toluene Conversion | % p-Xylene Selectivity |
|---|---|---|
| 3.17 | 11.12 | 81.01 |
| 20.67 | 7.01 | 94.13 |
| 27.17 | 6.99 | 95.40 |
| 92.67 | 3.23 | 94.98 |
| 99.17 | 3.14 | 95.44 |
| 116.67 | 8.77 | 96.82 |
| 123.17 | 10.00 | 97.04 |
| 140.67 | 9.42 | 97.14 |
| 147.17 | 8.22 | 97.07 |
| 164.67 | 9.09 | 97.45 |
| 171.17 | 9.38 | 97.60 |
| 188.67 | 9.11 | 97.63 |
| 195.17 | 9.15 | 97.66 |
| 284.67 | 7.82 | 97.62 |

As can be seen in FIG. 1, for Example 2 the level of selectivity for p-xylene remained fairly stable and also increased gradually over time. The conversion, however, decreased from 11 mole % to about 7 mole % during the first 27 hours. The conversion further decreased to about 3 mole % with the change in $H_2$/HC ratio change. The conversion then increased to about 9 mole % after the final $H_2$/HC ratio change. If the low conversion data taken at run time 93 and 99 hours are not taken into account the conversion remained fairly stable during the nearly 300 hours run time as shown in FIG. 2, Example 2. The toluene conversion (y) versus the time on stream (x) shows the following linear equation: y=−0.00003x+8.84, suggesting about 0.00003% conversion decrease per hour.

Example 3

A catalyst charge of 1.40 ml was loaded in the reactor. The catalyst was dried at about 200° C. under $H_2$ flow for at least 1 hour prior to feed introduction. The reactor pressure was maintained at about 20 psig. The toluene/methanol premixed feed with about a 2/1 mole ratio was introduced at a rate of about 0.182 ml/min giving an LHSV of about 8 $hr^{-1}$. The cofeed $H_2$ was used at 471 cc/min giving a $H_2$/HC mole ratio of about 8.0. The catalyst bed inlet temperature was slowly increased (10° C./min) and adjusted to about 500° C. The reactor operating conditions and toluene conversion and p-xylene selectivity are summarized in Tables 3A and 3B.

TABLE 3A

|  | Start-Up Conditions | Run Conditions |
|---|---|---|
| Temperature | 500° C. | 500° C. |
| Feed Toluene/Methanol Mole Ratio | 2:1 | 2:1 |
| LHSV, $hr^{-1}$ | 8 | 8 |
| H2/HC mole ratio | 8 | 8 |

TABLE 3B

| Time on Stream, hr | % Toluene Conversion | % p-Xylene Selectivity |
|---|---|---|
| 2.42 | 1.67 | 79.67 |
| 90.92 | 6.81 | 90.02 |
| 97.42 | 5.94 | 89.96 |
| 115.42 | 5.92 | 89.76 |
| 121.92 | 5.73 | 89.61 |
| 138.92 | 5.59 | 89.77 |

As can be seen more in FIGS. 1 and 2, for Example 3 the selectivity for p-xylene was around 90% level during the 139 hours run. The initial conversion was about 2%. Data taken during 91–139 hours time on stream showed that toluene conversion gradually decreased from about 7% to 6% with a 0.0203 average conversion decrease per hour.

Example 4

A catalyst charge of 2.70 ml was loaded in the reactor. The catalyst was dried at 200° C. under $H_2$ flow for at least 1 hour prior to feed introduction. The reactor pressure was maintained at 20 psig. The toluene/methanol premixed feed at a 1/1 mole ratio was introduced at a rate of about 0.088 ml/min giving an LHSV of about 2 $hr^{-1}$. The cofeed $H_2$ was used at 50 cc/min giving $H_2$/HC mole ratio of about 1.6. The catalyst bed inlet temperature was slowly increased (10° C./min) and adjusted to about 600° C. The reactor operating conditions and toluene conversion and p-xylene selectivity are summarized in Tables 4A and 4B.

TABLE 4A

|  | Start-Up Conditions | Run Conditions |
|---|---|---|
| Temperature | 600° C. | 600° C. |
| Feed Toluene/Methanol Mole Ratio | 1:1 | 1:1 |
| LHSV, $hr^{-1}$ | 2 | 2 |
| H2/HC mole ratio | 1.6 | 1.6 |

TABLE 4B

| Time on Stream, hr | % Toluene Conversion | % p-Xylene Selectivity |
|---|---|---|
| 3.60 | 7.86 | 88.11 |
| 21.10 | 14.05 | 92.81 |
| 27.60 | 12.11 | 93.17 |
| 94.10 | 12.36 | 93.30 |
| 99.60 | 10.75 | 93.35 |
| 117.10 | 11.77 | 93.39 |
| 123.60 | 10.44 | 93.37 |
| 141.10 | 9.60 | 93.33 |
| 147.60 | 7.12 | 93.30 |

As can be seen more in FIGS. 1 and 2, for Example 4 the level of selectivity for p-xylene remained fairly stable at around 93 mole % during the 148 hours run time. The initial conversion was about 8% and data taken during 21–148 hours time on stream the conversion gradually decreased from about 14% to 7%.

Comparative Example 5

A catalyst charge of 1.40 ml was loaded in the reactor, as described above. The catalyst was dried at 200° C. under $H_2$ flow for at least 1 hour prior to feed introduction. The reactor pressure was maintained at 20 psig. The toluene/methanol premixed feed with 2/1 mole ratio was introduced at a rate of about 3.18 ml/min giving an LHSV of about 135 $hr^{-1}$. The cofeed $H_2$ was used at 98 cc/min giving a $H_2$/HC mole ratio of about 0.1. The catalyst bed inlet temperature was slowly increased at about 10° C./min and adjusted to about 450° C. The reactor start-up and run operating conditions and toluene conversion and p-xylene selectivity are summarized in Tables 5A and 5B.

TABLE 5A

|  | Start-Up Conditions | Run Conditions |
|---|---|---|
| Temperature | 450° C. | 450° C. |
| Feed Toluene/Methanol Mole Ratio | 2:1 | 2:1 |
| LHSV, $hr^{-1}$ | 135 | 135 |
| H2/HC mole ratio | 0.1 | 0.1 |

TABLE 5B

| Time on Stream, hr | % Toluene Conversion | % p-Xylene Selectivity |
|---|---|---|
| 1.9 | 4.02 | 89.44 |
| 2.9 | 4.86 | 90.75 |
| 19.4 | 5.03 | 89.20 |
| 25.9 | 4.11 | 87.61 |
| 43.4 | 2.97 | 83.87 |
| 49.9 | 2.67 | 83.16 |

As can be seen more clearly in FIGS. 1 and 2, for Example 5 the level of selectivity for p-xylene dropped off fairly quickly, while the toluene conversion remained fairly level at 4–5 mole % during the first 26 hours and then the conversion decreased to about 3% within 50 hours of run time.

Comparative Example 6

A catalyst charge of 2.70 ml was loaded in the reactor. The catalyst was dried at 200° C. under $H_2$ flow for at least 1 hour prior to feed introduction. The reactor pressure was maintained at about 20 psig. The toluene/methanol premixed feed with 2/1 mole ratio was introduced at a rate of about 3.10 ml/min giving an LHSV of about 69 hr$^{-1}$. The cofeed H$_2$ was used at 98 cc/min giving H$_2$/HC mole ratio of about 0.1. The catalyst bed inlet temperature was slowly increased (10° C./min) and adjusted to about 500° C. After about 21 hours of run time, the feed rate was decreased to 1.56 ml/min giving LHSV of about 35 hr$^{-1}$. Also, cofeed H$_2$ cofeed gas rate was reduced from 98 cc/min to 49 cc/min to maintain H$_2$/HC mole ratio of about 0.1. The reactor operating conditions and toluene conversion and p-xylene selectivity are summarized in Tables 6A and 6B.

TABLE 6A

|  | Start-Up Conditions | Run Conditions (until 21 hr) | Run Conditions (21–52 hr) |
|---|---|---|---|
| Temperature | 500° C. | 500° C. | 500° C. |
| Feed Toluene/Methanol Mole Ratio | 2:1 | 2:1 | 2:1 |
| LHSV, hr$^{-1}$ | 69 | 69 | 35 |
| H2/HC mole ratio | 0.1 | 0.1 | 0.1 |

TABLE 6B

| Time on Stream, hr | % Toluene Conversion | % p-Xylene Selectivity |
|---|---|---|
| 2.65 | 13.68 | 94.97 |
| 3.65 | 13.66 | 95.40 |
| 21.15 | 6.24 | 94.14 |
| 27.65 | 5.00 | 93.25 |
| 45.15 | 2.44 | 88.17 |
| 51.65 | 2.44 | 87.88 |

As can be seen more clearly in FIGS. 1 and 2, for Example 6 the level of selectivity for p-xylene dropped off fairly quickly. The initial toluene conversion was about 14 mole % but decreased quickly to about 2 mole %.

In all the examples 1–6, the catalysts used were subsequently tested to determine if there was any structural aluminum loss during the toluene methylation reaction. This was done by first decoking the catalyst in a muffle furnace at 510° C. and the catalyst was analyzed by using solid state $^{27}$Al NMR. When compared to the fresh catalysts, the spent catalysts showed that there was little, if any, structural aluminum loss.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of preparing a xylene product comprising:
providing a reactor containing a phosphorus-treated ZSM-5-type zeolite catalyst;
initiating start-up of a toluene methylation reaction by contacting the catalyst with a toluene/methanol feed and a cofeed of hydrogen introduced into the reactor at start-up conditions wherein the toluene/methanol feed is introduced into the reactor at a liquid hourly space velocity (LHSV) of more than 5 hr$^{-1}$ and the cofeed of hydrogen is introduced at a hydrogen/(toluene+methanol) molar ratio of less than about 8;
operating the reactor at the start-up conditions for about one-half to about 20 hours; and then
operating the reactor at run conditions wherein the LHSV is reduced by at least 5 hr$^{-1}$ or more from the start-up LHSV to a run LHSV of 10 hr$^{-1}$ or less and the hydrogen/(toluene+methanol) molar ratio is at least 1.0.

2. The method of claim 1, wherein:
the phosphorus-treated ZSM-5-type zeolite catalyst having a total phosphorus content of from about 0.01 g P/g zeolite to about 0.15 g P/g zeolite.

3. The method of claim 1, wherein:
the start-up LHSV is from about 10 hr$^{-1}$ to about 50 hr$^{-1}$.

4. The method of claim 1, wherein:
the para-xylene content is at least 90% in the xylene product.

5. The method of claim 1, wherein:
the start-up hydrogen/(toluene+methanol) molar ratio is from about 0.1 to about 8.0.

6. The method of claim 1, wherein:
the reactor is operated at a pressure of from about 10 to about 50 psig.

7. The method of claim 1, wherein:
the toluene/methanol feed has a toluene/methanol molar ratio of from about 1:2 to about 10:1.

8. The method of claim 1, wherein:
the ZSM-5-type zeolite catalyst is treated with at least one of phosphoric acid and ammonium hydrogen phosphate.

9. The method of claim 1, wherein:
the reactor temperature is initially from 200° C. or above and upon introduction of the toluene/methanol feed the reactor temperature is gradually increased at a rate of 1 to 10° C./min to final start-up temperature from about 500° C. to about 700° C.

10. The method of claim 1, wherein:
the catalyst exhibits stable activity for at least 25 hours after start-up of the toluene methylation reaction.

11. The method of claim 1, wherein:
the catalyst has a silica/alumina mole ratio prior to phosphorus treatment from about 25 to about 300.

12. The method of claim 1, wherein:
there is substantially no structural aluminum loss of the catalyst during the toluene methylation reaction.

13. A method of preparing a xylene product comprising:
providing a reactor containing a phosphorus-treated ZSM-5-type zeolite catalyst using a silica/alumina mole ratio of from 25 to 300 prior to phosphorus treatment and a total phosphorus content of from about 0.01 g/g zeolite to about 0.15 g/g zeolite;
initiating start-up of a toluene methylation reaction by contacting the catalyst with a toluene/methanol feed and a cofeed of hydrogen introduced into the reactor at start-up conditions wherein the toluene/methanol feed is introduced into the reactor at a liquid hourly space velocity (LHSV) of from about 10 hr$^{-1}$ to about 90 hr$^{-1}$ and the cofeed of hydrogen is introduced at a hydrogen/(toluene+methanol) molar ratio of less than about 5;
operating the reactor at the start-up conditions for about one to about five hours; and then
operating the reactor at run conditions wherein the LHSV is reduced by 5 hr$^{-1}$ or more from the start-up LHSV to a run LHSV of 10 hr$^{-1}$ or less and the hydrogen/(toluene+methanol) molar ratio is increased from that of the start-up conditions.

14. The method of claim 13, wherein:
the start-up hydrogen/(toluene+methanol) molar ratio is from about 0.1 to about 8.0.

15. The method of claim 13, wherein:
the reactor is operated at a pressure of from about 10 to about 50 psig.

16. The method of claim 13, wherein:
the toluene/methanol feed has a toluene/methanol molar ratio of from about 1:2 to about 10:1.

17. The method of claim 13, wherein:
the ZSM-5-type zeolite catalyst is treated with phosphoric acid or ammonium hydrogen phosphate.

18. The method of claim 13, wherein:
the reactor temperature is initially from 200° C. or above and upon introduction of the toluene/methanol feed the reactor temperature is gradually increased at a rate of 1 to 10° C./min to final start-up temperature from about 500° C. to about 700° C., and maintaining the reactor temperature from about 500° C. to about 700° C.

19. The method of claim 13, wherein:
the catalyst exhibits stable activity for at least 500 hours after start-up of the toluene methylation reaction.

20. The method of claim 13, wherein:
the para-xylene content is at least 90% in xylene product.

21. A method of preparing a xylene product comprising:
providing a reactor containing a non-steamed, phosphorus-treated ZSM-5-type zeolite catalyst using a silica/alumina mole ratio of from 25 to 300 prior to phosphorus treatment and a total phosphorus content of from about 0.02 g/g zeolite to about 0.13 g/g zeolite;

initiating start-up of a toluene methylation reaction by contacting the catalyst with a toluene/methanol feed and a cofeed of hydrogen introduced into the reactor at start-up conditions wherein the toluene/methanol feed is introduced into the reactor at a liquid hourly space velocity (LHSV) of from about 10 hr$^{-1}$ to about 50 hr$^{-1}$ and the cofeed of hydrogen is introduced at a hydrogen/(toluene+methanol) molar ratio of less than about 8, and wherein the temperature is from about 500° C. to about 700° C.;

operating the reactor at the start-up conditions for about one to about two hours; and then operating the reactor at run conditions wherein the LHSV is reduced by 10 hr$^{-1}$ or more from the start-up LHSV to a run LHSV of 10 hr$^{-1}$ or less and the hydrogen/(toluene+methanol) molar ratio is increased by at least 2 and the temperature is from about 500° C. to about 700° C.; and wherein the catalyst exhibits stable activity for at least 500 hours after start-up of the toluene methylation reaction.

22. The method of claim 1, wherein:
the hydrogen/(toluene+methanol) molar ratio is increased by at least about 2 when switching from start-up conditions to run conditions.

23. The method of claim 13, wherein:
the hydrogen/(toluene+methanol) molar ratio is increased by at least about 2 when switching from start-up conditions to run conditions.

* * * * *